United States Patent [19]

Mizuno et al.

[11] Patent Number: 4,778,936
[45] Date of Patent: Oct. 18, 1988

[54] TRIPHENOL COMPOUND

[75] Inventors: Kenichi Mizuno; Yozo Jujo; Hajime Oyoshi, all of Iwakuni, Japan

[73] Assignee: Mitsui Petrochemical Industries, Ltd., Tokyo, Japan

[21] Appl. No.: 916,099

[22] Filed: Oct. 7, 1986

[30] Foreign Application Priority Data

Oct. 8, 1985 [JP] Japan .................................. 60-224305
Dec. 20, 1985 [JP] Japan .................................. 60-287288

[51] Int. Cl.⁴ ........................ C07C 39/12; C08G 63/64
[52] U.S. Cl. ...................................... 568/720; 528/196;
528/204; 568/722; 568/723; 568/729
[58] Field of Search ................. 568/720, 722, 723, 729

[56] References Cited

U.S. PATENT DOCUMENTS

| | | | |
|---|---|---|---|
| 3,309,339 | 3/1967 | Barton et al. | 568/720 |
| 3,544,514 | 12/1970 | Schnell et al. | 260/47 |
| 3,635,895 | 1/1972 | Kramer | 260/47 X |
| 3,644,538 | 2/1972 | Starnes | 568/720 |
| 3,925,488 | 12/1975 | Shin | 568/720 |
| 4,259,534 | 3/1981 | Gurvich et al. | 568/720 |
| 4,345,000 | 8/1982 | Kawazoe et al. | |
| 4,415,723 | 11/1983 | Hedges et al. | 528/204 |
| 4,426,513 | 1/1984 | Mark | 528/204 |
| 4,474,999 | 10/1984 | Mark et al. | 568/720 |

FOREIGN PATENT DOCUMENTS 0160159 2/1985 European Pat. Off. .
1532276 11/1978 United Kingdom .
2155193 9/1984 United Kingdom .

Primary Examiner—Harold D. Anderson
Attorney, Agent, or Firm—Cushman, Darby & Cushman

[57] ABSTRACT

A triphenol type compound represented by the following formula:

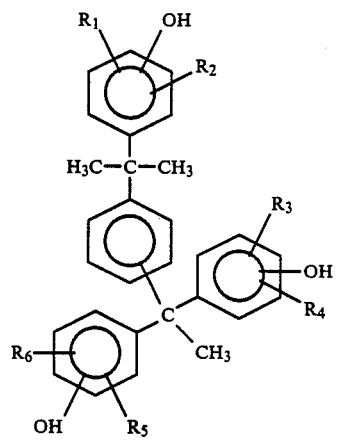

wherein $R_1$, $R_2$, $R_3$, $R_4$, $R_5$ and $R_6$ independently represent hydrogen, a halogen, a $C_1$–$C_5$ alkyl group or a $C_1$–$C_5$ alkoxy group.

The triphenol type compound can be used, as a branching agent for the production of a polycarbonate comprising (A) a carbonic acid component unit, (B) a divalent phenol component unit, and (C) a tripenol type compound component unit derived from the above-mentioned triphenol type compound. The triphenol type compound unit (C) is used in an amount of 0.01 to 10 mole %, based on the divalent phenol component unit (B) and the intrinsic viscosity [$\eta$], determined at 25° C. in methylene chloride, of the polycarbonate is 0.4 to 1.0 dl/g and the glass transition temperature (Tg), determined by a differential scanning type calorimeter is 150° C. to 300° C.

5 Claims, No Drawings

TRIPHENOL COMPOUND

BACKGROUND OF THE INVENTION

1. Field of the Invention

The present invention relates to a novel triphenol type compound. More particularly it relates to a novel triphenol type compound which is useful as a branching agent for polycarbonate. The present invention also relates to a novel polycarbonate and the production process thereof using the above-mentioned triphenol type compound as a branching agent.

2. Description of the Related Art

Polycarbonate is a synthetic resin which has been widely used in industry and is usually produced by the reaction between a divalent phenol such as 2,2-bis(4'-hydroxyphenyl)propane (hereinafter sometimes abbreviated as bisphenol A) and a carbonic acid derivative such as phosgene.

Although a polycarbonate produced from bisphenol A has excellent characteristics such as excellent impact resistance, small hygroscopicity, stable heat resistance and weathering resistance, since it behaves as a Newtonian fluid in a molten state, a great stress is required for obtaining a desired extruded amount and the melt elasticity or melt strength intimately correlated therewith is low, whereby a problem has arisen in that it is difficult to produce a large scale hollow molding.

To solve this problem, it has been proposed to permit a trivalent phenol such as phloroglucinol 4,6-dimethyl-2,4,6- tri(4'-hydroxyphenyl)heptene-2, 4,6-dimethyl-2,4,6-tri(4'-hydroxyphenyl) heptane or 2,6-bis(2'-hydroxy-5'-methylbenzyl)-4-methylphenol to be co-present in an amount of 0.01 mole % or more based on divalent phenol during production of polycarbonate, thereby branching the polycarbonate obtained, as disclosed in U.S. Pat. Nos. 3,635,895 or 3,544,514.

These thermoplastic branched polycarbonates obtained by permitting trivalent phenol to be co-present during the production of polycarbonate indeed exhibit non-Newtonian flow characteristics in a molten state, and their melts have an improved resistance to deformation. However, there are problems in that, compared with conventional polycarbonates prepared from bisphenol A, the moldings have an inferior color and transparency, and that resistance to deformation of the melt is not necessarily satisfactorily improved.

SUMMARY OF THE INVENTION

Accordingly, the objects of the present invention are to eliminate the above-mentioned disadvantages of the prior art and to provide a novel triphenol type compound which can provide a polycarbonate having excellent moldability and transparency by permitting the compound to be co-present in the reaction system in producing a polycarbonate by the reaction between a divalent phenol such as bisphenol A and a carbonic acid derivative such as phosgene.

Another object of the present invention is to provide a novel polycarbonate having excellent moldability and transparency.

A further object of the present invention is to provide a process for producing the above-mentioned polycarbonate having an excellent moldability and transparency.

Other objects and advantages of the present invention will be apparent from the following description.

In accordance with the present invention, there is provided a triphenol type compound represented by the following formula:

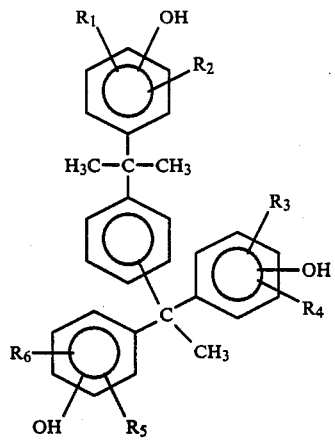

wherein $R_1$, $R_2$, $R_3$, $R_4$, $R_5$ and $R_6$, independently, represent hydrogen, a halogen, a $C_1$–$C_5$ alkyl group or a $C_1$–$C_5$ alkoxy group.

In accordance with the present invention, there is also provided a polycarbonate comprising (A) a carbonic acid component unit, (B) a divalent phenol component unit, and (C) a triphenol type compound component unit derived from the above-mentioned triphenol type compound. The amount of the triphenol type compound unit (C) is 0.01 to 10 mole %, based on the divalent phenol component unit (B) and the intrinsic viscosity [$\eta$], determined at 25° C. in methylene chloride, of the polycarbonate is 0.4 to 1.0 dl/g and the glass transition temperature (Tg), determined by a differential scanning calorimeter, is 150° C. to 300° C.

DESCRIPTION OF THE PREFERRED EMBODIMENTS

According to the present invention, the above-mentioned problems can be solved all at once by permitting a novel triphenol type compound having a specific structure to be co-present in production of a polycarbonate by the reaction between a divalent phenol such as bisphenol A and a carbonic acid derivative such as phosgene. Specific examples of the triphenol type compound represented by the formula [I] may include the following compounds:

1-[α-methyl-α-(4'-hydroxyphenyl)ethyl]-4-[α',α'-bis(4"-hydroxyphenyl)ethyl]benzene;

1-[α-methyl-α-(4'-hydroxyphenyl)ethyl]-3-[α',α'-bis(4"-hydroxyphenyl)ethyl]benzene;

1-[α-methyl-α-(3',5'-dimethyl-4'-hydroxyphenyl)ethyl]-4-[α',α'-bis(3",5"-dimethyl-4"-hydroxyphenyl)ethy]benzene;

1-[α-methyl-α-(3'-methyl-4'-hydroxyphenyl)ethyl]-4-[α',α'-bis(3"-methyl-4"-hydroxyphenyl)ethyl]benzene;

The triphenol type compound represented by the formula [I] can be produced by allowing isopropenylacetophenone to react with a phenolic compound according to the following scheme.

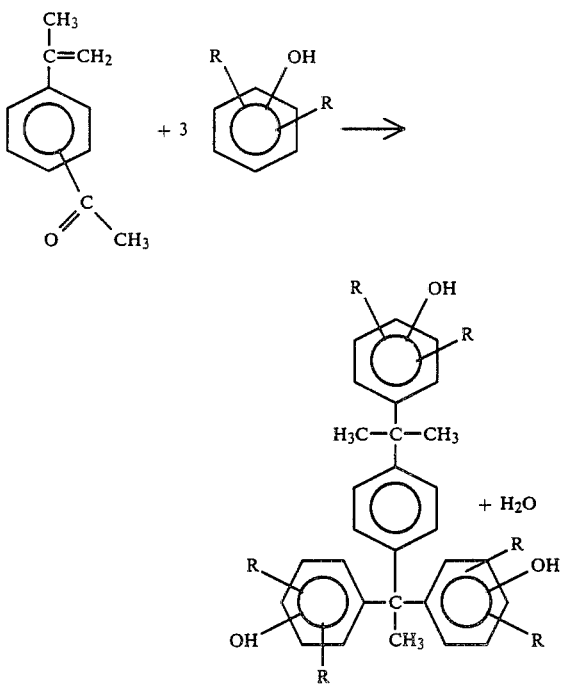

wherein each R may be the same or different from each other, and represents hydrogen, a halogen, a $C_1$-$C_5$ alkyl group or a $C_1$-$C_5$ alkoxy group. Examples of the isopropenylacetophenone usable in this reaction may include m-isopropenylacetophenone, p-isopropenylacetophenone or a mixture thereof.

Examples of the phenolic compound usable in this reaction may include phenol, o-cresol, m-cresol, p-cresol, 2,6-xylenol, o-methoxyphenol, m-methoxyphenol or a mixture thereof. When a mixture of the above phenolic compounds is used, it is possible to obtain a compound wherein all of the R's in the triphenol type compound represented by the formula [I] are different from each other.

The above reaction between isopropenyl acetophenone and a phenol can be carried out by, preferably, mixing an excess (e.g., 1.5 to 10 times) of the stoichiometric amount of a phenolic compound and an acid such as hydrogen chloride, sulfuric acid, hydorgen bromide, p-toluenesulfonic acid and cationic ion exchange resins as the catalyst, and adding isopropenyl acetophenone dropwise into the mixture obtained. The preferable amount of the catalyst is 0.03 to 1.0 parts by weight, based on 1.0 part by weight of the isopropenyl acetophenone. During this reaction, methylmercaptan or mercaptoacetic acid may be added, preferably up to 0.3 parts by weight, more preferably 0.01 to 0.3 parts by weight, based on 1.0 part by weight of the isopropenyl acetophenone, as a co-catalyst into the reaction system, if desired.

This reaction is carried out generally at a temperature range of from 40° C. to 80° C. at atmospheric pressure or elevated pressure (preferably 1 to 20 atm). The preferable reaction time is 1 to 100 hours. A triphenol type compound wherein R is a halogen in the above formula can be produced by using a phenolic compound in which the nucleus is substituted with a halogen as the starting material, or alternatively, it can be produced in some cases by halogenating a triphenol prepared from a phenolic compound having no halogen substituents.

For separation and purification of a triphenol type compound, which is the desired compound, from the reaction mixture, general methods such as extraction, concentration, crystallization, etc., can be used.

The structure of the triphenol type compound obtained is determined by, for example, mass spectrometry, proton nuclear magnetic resonance, and melting point.

The triphenol type compound according to the present invention is added to the reaction system in producing a polycarbonate by the reaction of a divalent phenol such as bisphenol A and a carbonic acid derivative such as phosgene, whereby a branched polycarbonate is obtained. The resultant branched polycarbonate has an amount of the triphenol type compound unit (C) of 0.01 to 10 mole % based on the divalent phenol component (B), an intrinsic viscosity ([η]), determined at 25° C. in methylene chloride, of 0.4 dl/g or higher, preferably 0.4 to 1.0 dl/g and a glass transition temperature, determined by a differential scanning type calorimeter, of 150° C. to 300° C., preferably 170° C. to 270° C., and has an excellent moldability and transparency. The transparency of the present polycarbonate is 80% or more against visible light at 420 nm when determined as mentioned below.

The triphenol type compound according to the present invention can be advantageously used in the reaction system for the production of a polycarbonate according to the reaction between a divalent phenol and carbonic acid derivatives such as phosgene in an amount of 0.01 to 10 mol %, preferably 0.01 to 3.0 mol % based on the divalent phenol. If the amount of triphenol type compound is less than 0.01 mol % based on the divalent phenol, the polycarbonate resin obtained does not exhibit the desired melt characteristic. On the other hand, if the amount exceeds 10 mol %, gelation may undesirably occur during production of the above resin or during molding of the resin.

Examples of the divalent phenol usable in production of polycarbonate may include bisphenol A, bis(4'-hydroxyphenyl)methane, 1,1-bis(4'-hydroxyphenyl)ethane, 1,1-bis(4'-hydroxyphenyl)cyclohexane, bis(4'-hydroxyphenyl)diphenylmethane, 1,1-bis(4'-hydroxyphenyl)-1-phenylethane, 2,2-bis(3',5'-dimethyl-4'-hydroxyphenyl)-propane, bis(4-hydroxyphenyl)ether, 4,4'-dihydroxydiphenyl, 3,3',5,5'-tetramethyl-4,4'-dihydroxydiphenyl, bis(4-hydroxyphenyl)sulfide, bis(4-hydroxyphenyl)sulfone, bis(4-hydroxyphenyl)sulfoxide, hydroquinone, resorcinol, or mixtures thereof. Of these phenols, bisphenol A is particularly preferred.

As the carbonic acid derivative to be reacted with a divalent phenol, a carbonyl halide such as phosgene, carbonyl fluoride, and carbonyl bromide, and diaryl carbonate, preferably phosgene, may be employed.

For producing a thermoplastic branched polycarbonate from a divalent phenol such as bisphenol, a carbonic acid derivative such as phosgene, and a triphenol type compound according to the present invention, other than permitting a triphenol type compound to be co-present in the reaction system of a divalent phenol and a carbonic acid derivative such as phosgene, it is possible to use the methods known in the art. Examples of such methods are shown below as (a) to (c). These methods are carried out under conventional reaction conditions.

(a) The method in which a divalent phenol and a triphenol type compound according to the present invention are dissolved in an organic base such as pyridine or triethylamine, and the reaction is carried out by blowing a carbonic acid derivative into this solution.

(b) The method in which a divalent phenol and a triphenol type compound according to the present invention are allowed to react with a carbonic acid derivative such as phosgene in the presence of an inert solvent such as methylene chloride, chlorobenzene, toluene, etc., and an acid acceptor such as pyridine, etc.

(c) The method in which the reaction is carried out by blowing a carbonic acid derivative into an aqueous solution or slurry of alkyl metal salts of a divalent phenol and a triphenol type compound according to the present invention in the presence of an inert solvent such as methylene chloride, ethylene dichloride, chlorobenzene, etc., generally in the co-presence of a phase transfer catalyst such as a tertiary amine or a quaternary ammonium salt.

In any of these methods, the triphenol type compound of the present invention can be added together with the divalent phenol from the beginning of the polymerization reaction. Also, in any of these methods, it is possible to add 1 to 10 mol % based on the divalent phenol of a monovalent phenol such as phenol, p-tert-butylphenol, p-cumylphenol, etc., as the terminator.

Also, as an alternative method for producing a polycarbonate, the method may be employed in which a divalent phenol and a triphenol type compound according to the present invention are allowed to react with a diaryl carbonate in the presence of an ester exchange catalyst such as a metal oxide.

The branched polycarbonate produced by using triphenol type compound according to the present invention is thermoplastic and can be easily processed into a molded article with a desired shape according to conventional molding methods such as extrusion molding, blow molding, etc., from its melt. Also, it is soluble in specific organic solvents, and the solution can be processed into a molded article such as a film.

The branched polycarbonate produced by using of a triphenol type compound according to the present invention also can be used as a mixture with other polycarbonates or thermoplastic polyesters. Further, if desired, the above polycarbonate can be used as a mixture with fillers such as glass fibers, stabilizers, flame retardants or blowing agents.

According to the present invention, as mentioned above, a novel triphenol type compound is obtained, and by permitting this triphenol type compound to be copresent in the reaction system for production of a polycarbonate by the reaction between a divalent phenol such as bisphenol A and a carbonic acid derivative such as phosgene, the branched polycarbonates which have an excellent moldability and transparency are obtained.

EXAMPLES

The present invention will now be further illustrated by, but is by no means limited to, the following Examples. The preparation of the triphenol type compounds in the following Examples was carried out at atmospheric pressure.

EXAMPLE 1

Preparation of 1-[α-methyl-α-(4'-hydroxyphenyl)-ethyl]-4-[α',α'-bis(4"-hydroxyphenyl)ethyl]benzene from p-isopropenylacetophenone and phenol:

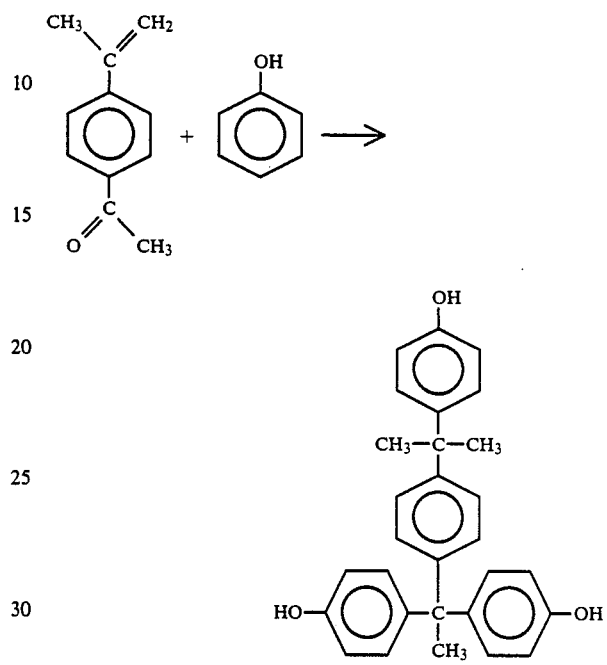

(1) Into a 500 ml round-bottomed flask equipped with a stirrer, a dropping funnel, a thermometer, a reflux condenser and a gas blowing pipe, were charged 194 g of phenol and 4 g of 15 wt. % aqueous methylmercaptan sodium salt solution, and after heating to 40° C., dry hydrogen chloride gas was blown through a gas charging pipe under stirring until the system was internally saturated. Subsequently, a mixture of 32 g of p-isopropenylacetophenone and 32 g of phenol was added dropwise through a dropping funnel over 2 hours. During this period, the reaction temperature was maintained at 40° to 43° C., and the blowing of dry hydrogen chloride gas was also continued. After completion of the dropwise addition, stirring was continued at a temperature of 40° to 43° C. while blowing, little by little, dry hydrogen chloride gas for an additional 8 hours.

(2) The reaction mixture obtained was left to stand overnight at room temperature, then added with 1200 g of toluene and 600 g of 3 wt. % agueous sodium hydrogen carbonate solution, and the mixture was stirred at 80° C. for 30 minutes, followed by cooling of the whole mixture as such to room temperature. The precipitated crystals were separated by a centrifugal machine, and the crystals were washed with toluene and then with H₂O. Further, the crystals were dissolved in a heated solvent mixture of methyl isobutyl ketone-toluene, washed with water and then cooled to precipitate crystals again. The crystals were separated to obtain 70.8 g of white crystals melting at 222°-225° C. The crystals were identified from the results of mass spectrometry and proton nuclear magnetic resonance to be 1-[α-methyl-α-(4'-hydroxyphenyl)ethyl]-4-[α',α'-bis(4"-hydroxypheny-1)ethyl]benzene having the following formula:

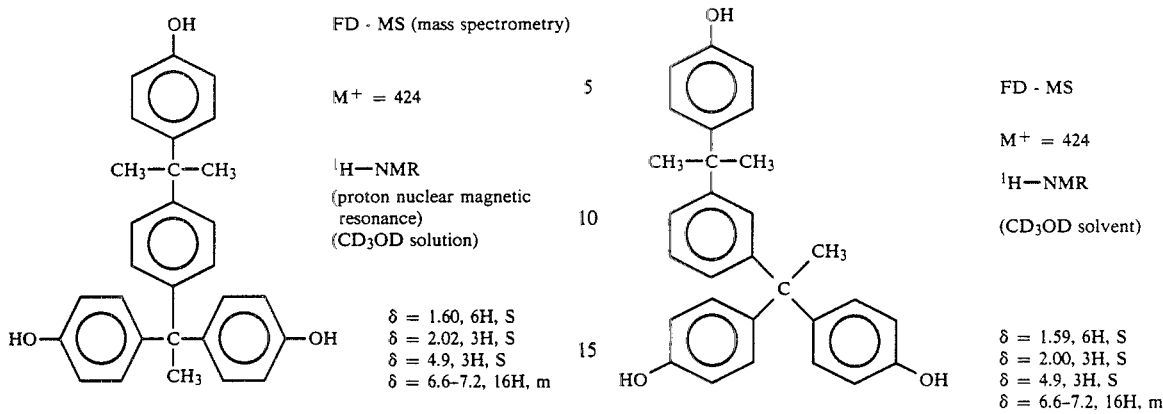

FD - MS (mass spectrometry)

M+ = 424

¹H—NMR
(proton nuclear magnetic resonance)
(CD₃OD solution)

δ = 1.60, 6H, S
δ = 2.02, 3H, S
δ = 4.9, 3H, S
δ = 6.6–7.2, 16H, m

FD - MS

M+ = 424

¹H—NMR
(CD₃OD solvent)

δ = 1.59, 6H, S
δ = 2.00, 3H, S
δ = 4.9, 3H, S
δ = 6.6–7.2, 16H, m

EXAMPLE 2

Preparation of 1-[α-methyl-α-(4'-hydroxyphenyl)-ethyl]-3-[α',α'-bis(4''-hydroxyphenyl)-ethyl]benzene from m-isopropenylacetophenone and phenol:

EXAMPLE 3

Preparation of 1-[α-methyl-α-(3', 5'-dimethyl-4'-hydroxyphenyl)ethyl]-4-[α',α'-bis(3'', 5''-dimethyl-4''-hydroxyphenyl)ethyl]benzene from p-isopropenylacetophenone and 2,6-xylenol:

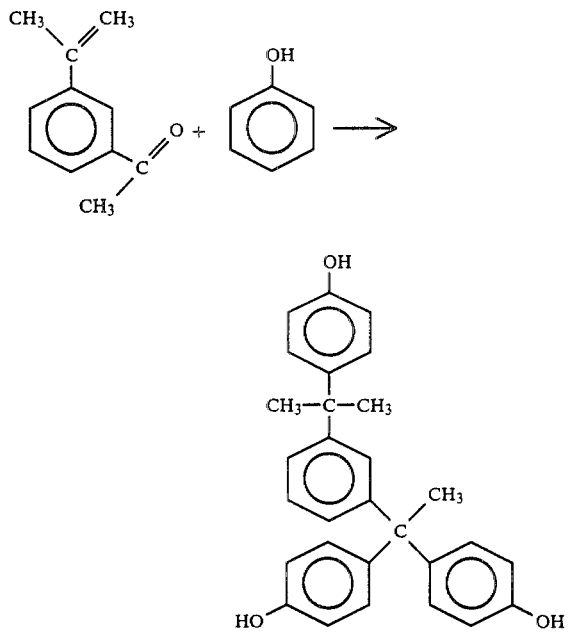

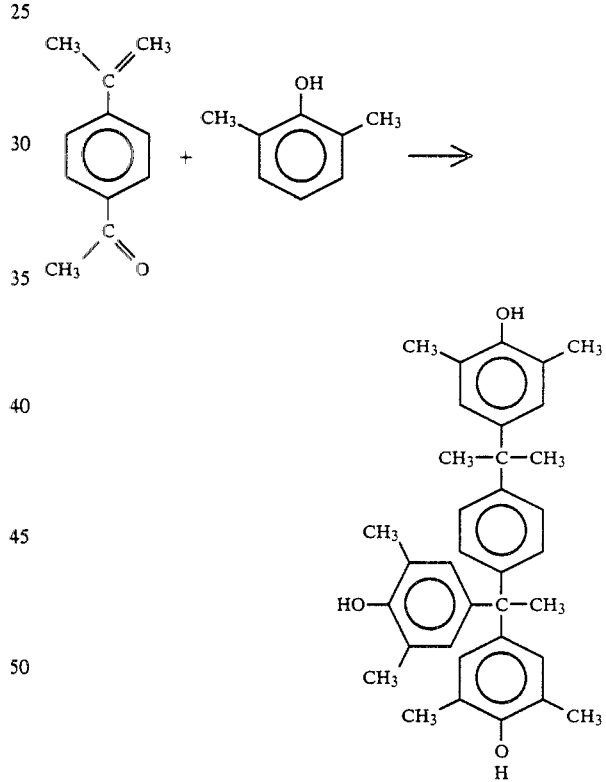

(1) The reaction was carried out according to the same procedure as described in Example 1(1) except for using m-isopropenylacetophenone in place of p-isopropenylacetophenone.

(2) The reaction mixture obtained was dissolved in 640 g of toluene, washed with 3 wt. % aqueous NaHCO₃ solution and then with a dilute aqueous phosphoric acid solution, followed by evaporation of the toluene and unreacted phenol under a reduced pressure. The residue obtained was recrystallized from toluene to obtain 69.3 g of white crystals. The crystals exhibited a melting point of 187°–189° C. and were identified from the results of mass spectrometry and proton nuclear magnetic resonance to be 1-[α-methyl-α-(4'-hydroxyphenyl)ethyl]-3-[α',α'-bis(4''-hydroxyphenyl)ethyl]benzene having the following formula:

(1) Into the reactor as shown in Example 1(1) were charged 228 g of 2,6-xylenol, 5.8 g of 15 wt. % aqueous methylmercaptan sodium salt solution and 56 g of concentrated hydrochloric acid, and the mixture was heated to 50° C. Under stirring, while blowing dry hydrogen chloride gas through the gas blowing pipe, a mixture of 32 g of p-isopropenylacetophenone and 64 g of 2,6-xylenol was added dropwise over 2 hours. During this period, the reaction temperature was maintained at 46° to 48° C. After completion of the dropwise addition, stirring was continued at 46° to 48° C. while blowing dry hydrogen chloride gas for 70 hours to complete the reaction.

(2) To the reaction mixture obtained was added 400 g of toluene and the mixture was heated to 80° C. After the separated aqueous layer was removed, the oil layer was washed with 3 wt. % aqueous NaHCO₃ solution and then with a dilute aqueous phosphoric acid solution. After toluene and unreacted 2,6-xylenol were evaporated under a reduced pressure from the oil layer, the residue was recrystallized twice from toluene to obtain 67.1 g of white crystals. The crystals exhibited a melting point of 191°–194° C. and were identified from the results of mass spectrometry and proton nuclear magnetic resonance to be 1-[α-methyl-α-(3′,5′-dimethyl-4′-hydroxyphenyl)ethyl]-4-[α′,α′-bis(3″,5″-dimethyl-4″-hydroxyphenyl)ethyl]benzene having the following formula:

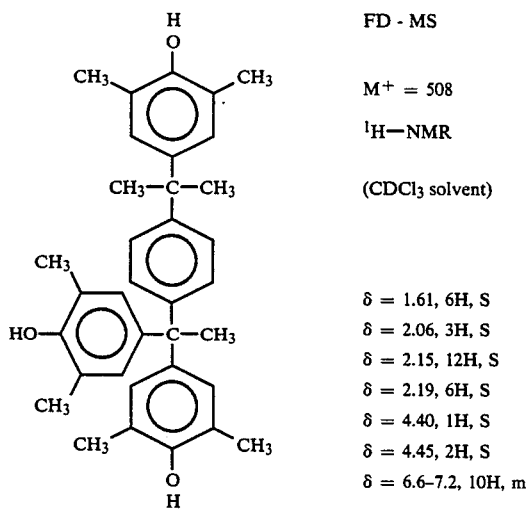

FD - MS

M⁺ = 508

¹H—NMR (CDCl₃ solvent)

δ = 1.61, 6H, S
δ = 2.06, 3H, S
δ = 2.15, 12H, S
δ = 2.19, 6H, S
δ = 4.40, 1H, S
δ = 4.45, 2H, S
δ = 6.6–7.2, 10H, m

EXAMPLE 4

Preparation of 1-[α-methyl-α-(3′-methyl-4′-hydroxyphenyl)ethyl]-4-[α′,α′-bis(3″-methyl-4″-hydroxyphenyl)-ethyl]benzene from p-isopropenylacetophenone and o-cresol:

(1) The reaction was carried out according to the same procedure as described in Example 1(1) except that 227 g of o-cresol was used instead of phenol.

(2) The reaction mixture obtained was dissolved in 500 g of toluene, washed with 3 wt. % aqueous NaHCO₃ solution and then with dilute aqueous phosphoric acid solution, followed by evaporation of the toluene and unreacted o-cresol under a reduced pressure.

The residue obtained was recrystallized from decane to obtain 69.8 g of pale yellow solids. The solid exhibited a melting point of 87°–91° C. and was identified from the results of mass analysis and proton nuclear magnetic resonance to be 1-[α-methyl-α-(3′-methyl-4′-hydroxyphenyl)ethyl]- 4-[α′,α′-bis(3′- methyl-4′-hydroxyphenyl)ethyl]benzene having the following formula:

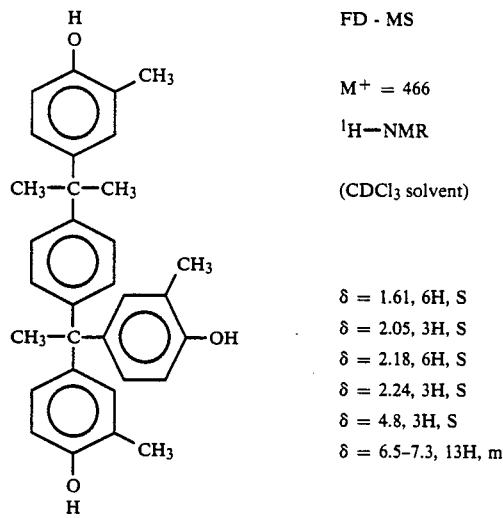

FD - MS

M⁺ = 466

¹H—NMR (CDCl₃ solvent)

δ = 1.61, 6H, S
δ = 2.05, 3H, S
δ = 2.18, 6H, S
δ = 2.24, 3H, S
δ = 4.8, 3H, S
δ = 6.5–7.3, 13H, m

EXAMPLE 5

Preparation of thermoplastic branched polycarbonate by using the triphenol compound obtained in Example 1:

(1) While a mixture of 228 g (1 mol) of bisphenol A, 4.9 g of p-tert-butylphenol, 4.24 g (0.01 mol) of 1-[α-methyl-α-(4′-hydroxyphenyl)-ethyl]-4-[α′,α′-bis(4″-hydroxyphenyl)ethyl]benzene, 1375 g of 9 wt. % aqueous sodium hydroxide solution and 2300 g methylene chloride was stirred under an N₂ atmosphere at 20° to 25° C., 121 g of phosgene was blown thereinto for 2 hours. After completion of the phosgene blowing, 0.4 g of triethylamine was added and stirring was further continued for 1 hour. Then, stirring was stopped and the separated aqueous layer was removed to obtain an organic layer containing a polycarbonate.

The organic layer was washed 3 times alternately with 2 wt. % aqueous caustic soda solution and with 2 wt. % aqueous phosphoric acid solution, and further washed 10 times with distilled water, then 500 g of chlorobenzene was added and methylene chloride was removed by distillation. The polycarbonate precipitated after cooling was separated and dried in vacuo at 120° C. for 48 hours.

The intrinsic viscosity ([η]) of the polycarbonate obtained in methylene chloride at 25° C. is shown in Table 1, and the properties thereof in Table 2, Table 3, Table 4, and Table 5.

EXAMPLE 6

A thermoplastic branched polycarbonate was prepared according to the same procedure as described in Example 5, except for using 4.24 g of 1-[α-methyl-(4′-hydroxyphenyl)ethyl]-3-[α′,α′-bis(4″-hydroxyphenyl)-ethyl]benzene obtained in Example 2 in place of the compound obtained in Example 1 as the triphenol compound.

The intrinsic viscosity ([η]) of the polycarbonate obtained in methylene chloride at 25° C. is shown in Table 1, and the properties thereof in Table 2, Table 3, Table 4, and Table 5.

EXAMPLES 7–8

Polycarbonates were prepared according to the same procedure as described in Example 5, except for using 5.08 g of 1-[α-methyl-α-(3',5'-dimethyl-4'-hydroxyphenyl)ethyl]-4-[α',α'-bis-(3'',5''-dimethyl-4'-hydroxyphenyl)ethyl]benzene obtained in Example 3 (Example 7) and 4.66 g of 1-[α-methyl-α-(3'-methyl-4''-hydroxyphenyl)ethyl]-4-[α',α'-bis(3''-methyl-4''-hydroxyphenyl)ethyl]benzene obtained in Example 4 (Example 8) in place of the compound obtained in Example 1 as the triphenol compound. The intrinsic viscosities ([η]) of the polycarbonates obtained in methylene chloride at 25° C. are shown in Table 1, and their properties in Table 2, Table 3, Table 4, and Table 5.

COMPARATIVE EXAMPLES 1-3

Polycarbonates were prepared according to the same procedure as described in Example 5, except for using 1.26 g of phluoroglucinol (Comparative Example 1), 3.48 g of 2,6-bis(2'-hydroxy-5'-methylbenzyl)-4-methylphenol (Comparative Example 2) or 4.02 g of 4,6-dimethyl-2,4,6-tri(4'-hydroxyphenyl)heptene-2 (Comparative Example 3), instead of the compound obtained in Example 1 as the triphenol compound. The intrinsic viscosities ([η]) of the polycarbonates obtained in methylene chloride at 25° C. are shown in Table 1, and their properties in Table 2, Table 3, Table 4, and Table 5.

The transparency of polycarbonate was evaluated as follows. That is, each of the polycarbonates obtained in Reference Examples 5 to 8 and Comparative Examples 1 to 3 was molded at 300° C. to prepare a pressed sheet with a thickness of 0.3 mm. For this pressed sheet, the light transmittance of visible light at 420 nm was measured as transparency of the polycarbonate.

On the other hand, the melt index ratio of a polycarbonate indicates the non-Newtonian characteristics of the polycarbonate resin, and the melt index ratio at 300° C. of each of the polycarbonates obtained in Examples 5 to 8 and Comparative Examples 1 to 3 was determined from the following formula.

$$\text{Melt index ratio} = \frac{\text{Grams of polycarbonate extruded for 10 minutes when a pressure of 21.6 kg is applied on a piston}}{\text{Grams of polycarbonate extruded for 10 minutes when a pressure of 2.16 kg is applied on a piston}} \times \frac{1}{10}$$

Further, the melt characteristics of polycarbonate were measured by extruding each of the polycarbonates obtained in Examples 5 to 8 and Comparative Examples 1 to 3 through an exturder (heating zones 290° C., 290° C., 290° C., 220° C.; screw rotational number 18 rpm) to prepare a strand with a length of 50 cm, and represented in terms of the time required for extrusion and the weight of the strand.

TABLE 1

| | Intrinsic viscosity ([η]) of polycarbonate (in methylene chloride, 25° C.) | | |
|---|---|---|---|
| Example | [η], dl/g | Comparative Example | η, dl/g |
| 5 | 0.614 | 1 | 0.583 |
| 6 | 0.608 | 2 | 0.591 |
| 7 | 0.591 | 3 | 0.587 |
| 8 | 0.589 | | |

TABLE 2

| Transparency (light transmittance) of polycarbonate | | | |
|---|---|---|---|
| Example | Light transmittance (%) | Comparative Example | Light transmittance (%) |
| 5 | 84 | 1 | 68 |
| 6 | 83 | 2 | 73 |
| 7 | 81 | 3 | 72 |
| 8 | 82 | | |

TABLE 3

| Melt index ratio | | | |
|---|---|---|---|
| Example | Melt index ratio | Comparative Example | Melt index ratio |
| 5 | 3.4 | 1 | 2.8 |
| 6 | 3.4 | 2 | 2.7 |
| 7 | 3.6 | 3 | 2.8 |
| 8 | 3.5 | | |

TABLE 4

| | Melt characteristics | |
|---|---|---|
| | Extrusion of strand with 50 cm length | |
| | Time (sec) | Weight (g) |
| Example | | |
| 5 | 92 | 87 |
| 6 | 93 | 86 |
| 7 | 95 | 89 |
| 8 | 93 | 88 |
| Comparative Example | | |
| 1 | 90 | 79 |
| 2 | 88 | 75 |
| 3 | 86 | 74 |

TABLE 5

| Glass transition temperature Tg (°C.) | | | |
|---|---|---|---|
| Example | Tg | Comparative Example | Tg |
| 5 | 238 | 1 | 207 |
| 6 | 235 | 2 | 217 |
| 7 | 218 | 3 | 210 |
| 8 | 221 | | |

EXAMPLES 9-11

Triphenol type compounds were prepared in the same manner as in Example 3 except for using the compounds shown in Table 6 in place of 2,6-xylenol as the phenol compound of the starting material to obtain triphenol type compounds as shown in Table 7.

TABLE 6

Starting phenol compounds

OH
R₁—⌬—R₂

| Example | $R_1$ | $R_2$ |
|---|---|---|
| 9 | 2-Et | 6-Et |
| 10 | 2-OMe | H |
| 11 | 2-Cl | H |

TABLE 7

Triphenol type compound

TABLE 7-continued

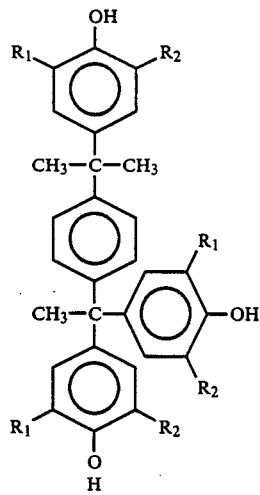

| Example | R₁ | R₂ |
|---------|-----|-----|
| 9 | Et | Et |
| 10 | OMe | H |
| 11 | Cl | H |

EXAMPLES 12–14

Polycarbonates were prepared in the same manner as in Example 5 except for using the triphenol type compounds obtained in Examples 9–11 in amounts of 1 mol % based on bisphenol A in place of the compound obtained in Example 1 as the triphenol type compound. Thermoplastic branched polycarbonates containing the corresponding triphenol type compounds as branched components were obtained.

We claim:

1. A triphenol compound represented by the following formula:

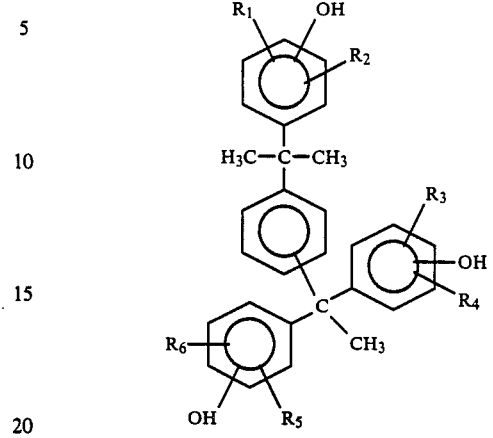

wherein $R_1$, $R_2$, $R_3$, $R_4$, $R_5$ and $R_6$, independently, represent hydrogen, a halogen, a $C_1$–$C_5$ alkyl group or a $C_1$–$C_5$ alkoxy group.

2. A compound as claimed in claim 1, wherein the triphenol compound is 1-[α-methyl-α-(4′-hydroxyphenyl)ethyl]-4-[α′,α′-bis(4″-hydroxyphenyl)ethyl]benzene.

3. A compound as claimed in claim 1, wherein the triphenol compound is 1-[α-methyl-α-(4′-hydroxyphenyl)ethyl]-3-[α′,α′-bis(4″-hydroxyphenyl)ethyl]benzene.

4. A compound as claimed in claim 1, wherein the triphenol compound is 1-[α-methyl-α-(3′-methyl-4′-hydroxyphenyl)ethyl]-4-[α′,α′-bis(3″-methyl-4″-hydroxyphenyl)ethyl]benzene.

5. A compound as claimed in claim 1, wherein the triphenol compound is 1-[α-methyl-α-(3′,5′-dimethyl-4′-hydroxyphenyl)ethyl]-4-[α′,α′- bis(3″,5″-dimethyl-4″-hydroxyphenyl)ethyl]benzene.

* * * * *